United States Patent
King

(10) Patent No.: US 6,446,814 B1
(45) Date of Patent: Sep. 10, 2002

(54) METHOD OF MAKING A DUAL FILTER

(76) Inventor: Joseph A. King, 142 Chevy Chase Dr., Wayzata, MN (US) 55391

( * ) Notice: Subject to any disclaimer, the term of this patent is extended or adjusted under 35 U.S.C. 154(b) by 0 days.

(21) Appl. No.: 09/550,668

(22) Filed: Apr. 17, 2000

Related U.S. Application Data

(60) Provisional application No. 60/130,468, filed on Apr. 22, 1999.

(51) Int. Cl.⁷ .............................. B01D 39/08
(52) U.S. Cl. ............ 210/501; 210/504; 210/506; 210/508
(58) Field of Search ................ 210/501, 504, 210/506, 508

(56) References Cited

U.S. PATENT DOCUMENTS

| | | | |
|---|---|---|---|
| 3,327,859 A | * | 6/1967 | Pall |
| 3,872,013 A | | 3/1975 | Nishino et al. ............. 210/317 |
| 4,071,636 A | * | 1/1978 | Nishino |
| 4,116,738 A | | 9/1978 | Pall ............................ 156/167 |
| 4,992,311 A | * | 2/1991 | Hisazumi et al. .......... 428/35.4 |
| 5,064,534 A | | 11/1991 | Brusch et al. .............. 210/266 |
| 5,185,415 A | | 2/1993 | Kawabata et al ........... 526/265 |
| 5,338,340 A | | 8/1994 | Kasmark, Jr. et al. ....... 96/135 |
| 5,438,083 A | * | 8/1995 | Takimoto et al. ............ 523/401 |
| 5,965,233 A | * | 10/1999 | Tojo et al. ................... 428/141 |
| 6,143,419 A | * | 11/2000 | Hanada et al. .............. 428/195 |
| 6,159,605 A | * | 12/2000 | Hanada et al. .............. 428/195 |
| 6,165,243 A | * | 12/2000 | Kawaguchi |
| 6,264,321 B1 | * | 7/2001 | Bugner et al. ............... 347/101 |

FOREIGN PATENT DOCUMENTS

| | | | |
|---|---|---|---|
| DE | 37 19 233 | 12/1988 | .......... B01D/39/16 |
| EP | 0 804 877 | 11/1997 | .......... A01N/59/16 |
| EP | 0 911 297 | 4/1999 | ............. C02F/1/50 |

* cited by examiner

*Primary Examiner*—Chester Berry
(74) *Attorney, Agent, or Firm*—Jacobson & Johnson

(57) ABSTRACT

A dual filter apparatus and a process of making a dual filter apparatus that minimizes disruption to the normal flow pattern through the filter apparatus by forming a porous medium suitable to carry a water treatment composition thereon and placing a bacteria killing material proximate the porous filter medium for in situ killing of bacteria and removal of debris from the water by screening action of the porous filter medium that entraps debris thereon.

8 Claims, 8 Drawing Sheets

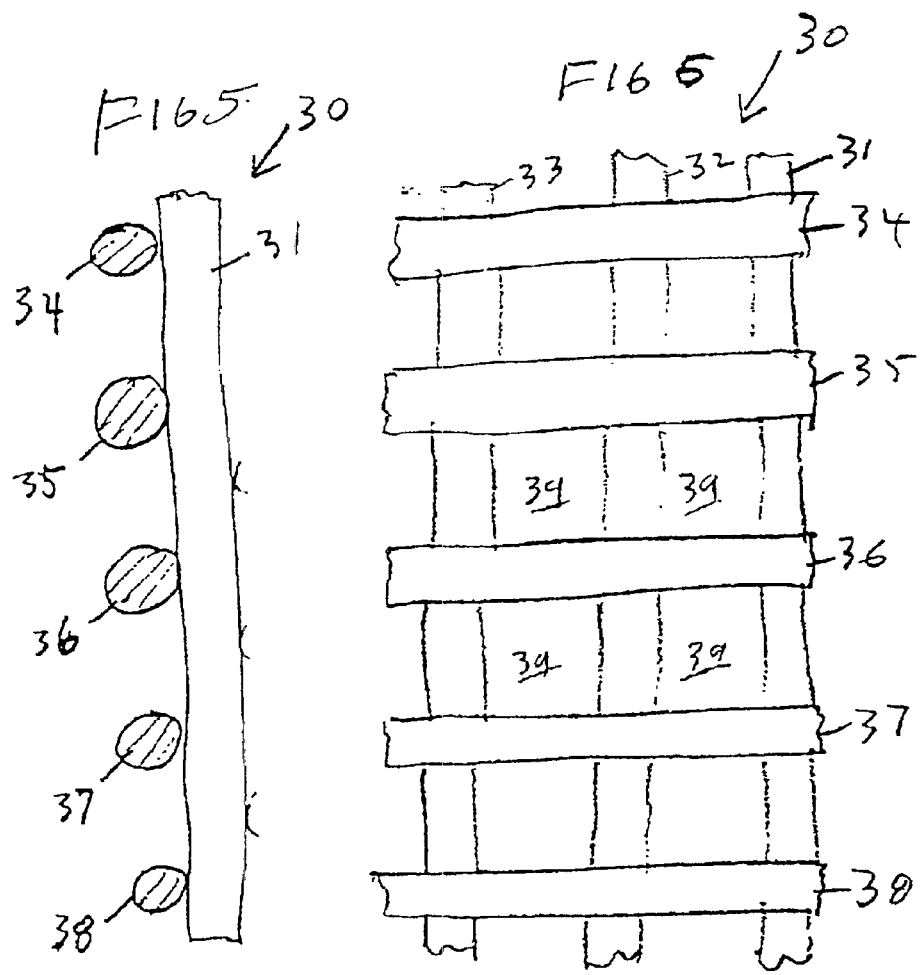
FIG 5
FIG 6
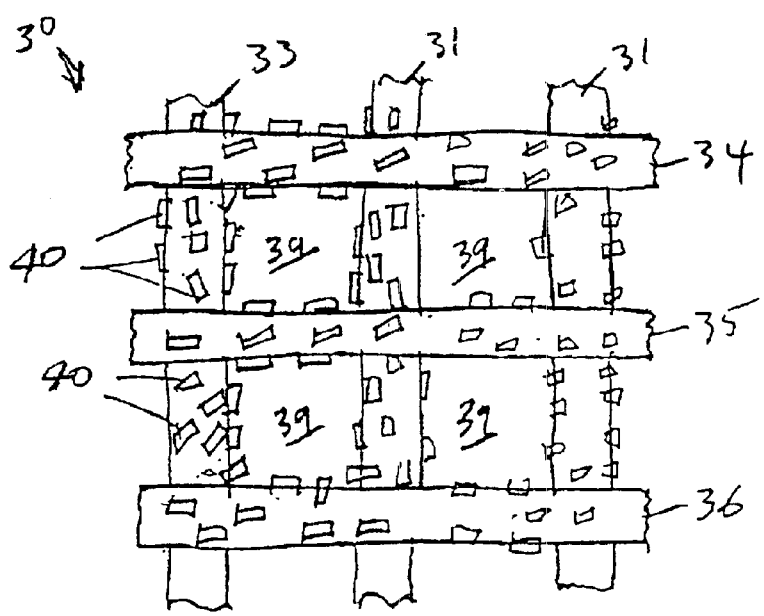
FIG 7

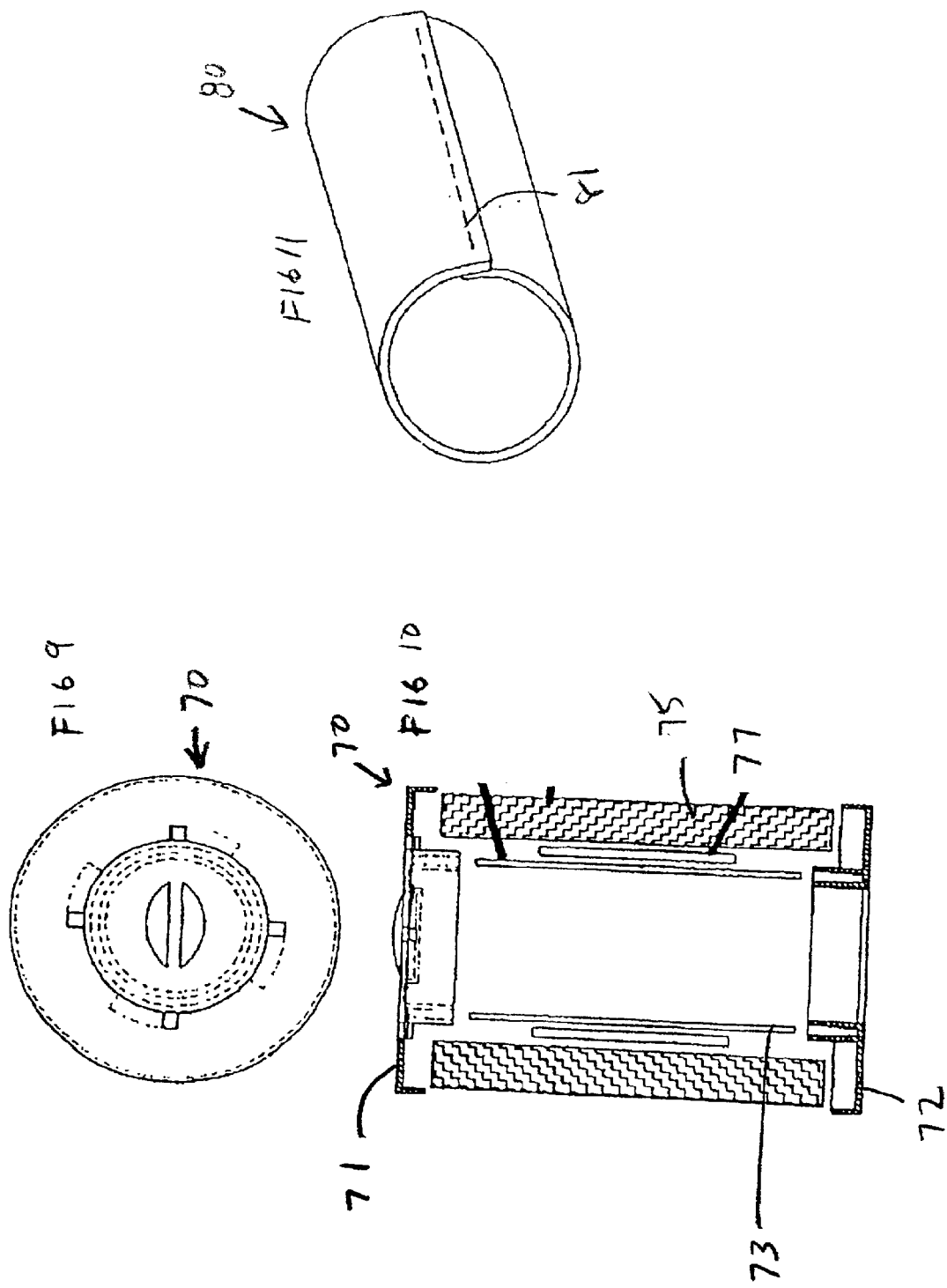

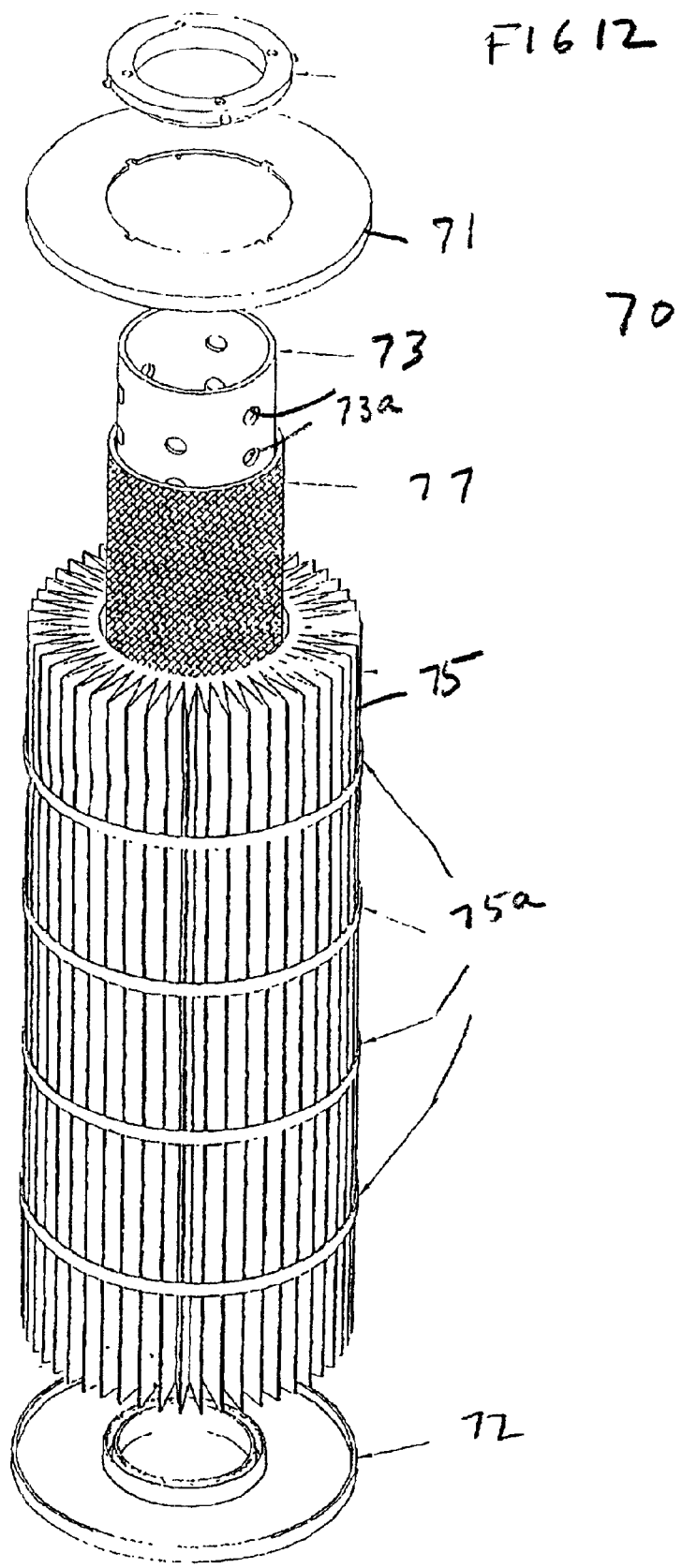

METHOD OF MAKING A DUAL FILTER

CROSS REFERENCE TO RELATED APPLICATIONS

This application claims priority from my co-pending U.S. patent application Ser. No. 08/957,265, filed Oct. 24, 1997, titled Water Treatment Composition, co-pending U.S. patent application Ser. No. 08/719,482 filed Sep. 25, 1996 titled Nestable containers and improved water treatment materials and co-pending Provisional patent application No. 60/130,468 titled Dual Filter and Method of Making, filed Apr. 22, 1999.

FIELD OF THE INVENTION

This invention relates generally to a dual filter system and apparatus and more specifically to a replaceable water filter carrying a water purification composition dispersibly secured therein to enable the water filter to simultaneously and in situ purify water as water flows through the water filter while minimizing disruption to the normal flow of water through the filter system.

BACKGROUND OF THE INVENTION

In water treatment systems it is known that bacteria killing materials such as metal ions are effective in killing bacteria. One commonly used metal ion is the silver ion and another commonly used bacteria killing and material is the zinc ion. Other types of ions are used as algaecides. The difficulty in use of metal ions is to maintain the ion concentration within proper ranges since too low metal ion concentration results in ineffective killing of bacteria and to high metal ion concentrations can be harmful. Another difficulty is to be able to controllable release the materials to provide for water purification over an extended period of time.

It has been demonstrated that a single bacteria killing material that releases silver ions can be effectively used to kill bacteria in water systems such as spas, hot tubs and swimming pools over an extended period of time. In some cases multiple bacteria killing materials that releases both ions of silver and zinc are used to kill bacteria over an extended period of time.

In one embodiment of a bacteria killing material I use an adhesive that is securable to both a metal ion generating material and to a particle carrier that is placed in a container within the water supply. Water is allowed to flow through the container as the bacteria killing material controllable release metal ions to kill bacteria in the water. While the use of bacteria killing materials that release metal ions is known, the present invention is directed to the structure and mechanism for holding the bacteria killing materials so as not to interfere with the release of the bacteria killing materials such as metal ions without disrupting the normal flow of water through the system.

In most recirculation systems such as for swimming pools, spas and hot tubs a filter is included that removes unwanted waste particles from the water. In one embodiment, which is shown in U.S. Pat. No. 4,780,197 a container is placed in the core of the filter. The container is filled with a bacteria killing material such as chlorine or bromine. In this type of arrangement one can provide for removal of waste particles as well as killing of bacteria in the same part of the system. While this type of system brings the bacteria killing and water purification into the filter housing it does not provide for in situ killing of bacteria and removal of debris. However, more importantly, devices placed in the core of the filter create obstructions to normal flow though the fluid filter. The first obstruction to normal flow is the container itself which hold the bactericide and the second obstruction to normal flow is the materials that are placed in the container. In the present invention the obstruction to normal flow of water through the filter system is substantially eliminated as the bacteria killing material is either secured directly to the filter medium or to a portion of the filter where the flow area is generally the largest thereby allowing one to maintain the normal flow patterns of the filter mechanism.

In the present invention, a water treatement composition, for example, a water purification material, such as a bacteria killing material is secured to a replaceable filter that normally removes debris from the water. With the present invention the replaceable filter performs a dual in situ function in that the filter simultaneously removes debris and kills bacteria. Consequently, when the filter is replaced due to accumulation of debris thereon the bacteria killing material is replaced in the same operation thus minimizing the consumer maintenance in maintaining a water system in proper condition. Thus the present invention becomes consumer friendly as the need for maintenance of the system can be reduced.

In one embodiment of the dual filter apparatus of the present invention, a bacteria killing material is affixed directly to fibers that are formed into a filter medium with the fibers formed into a network for screening removal of debris from the water. As water is directed through the filter medium formed from the fibers containing the bacteria killing material the filter medium traps debris thereon, while the bacteria killing material kills bacteria thereon. In this embodiment the dual filter apparatus simultaneously accomplishes the in situ task of both filtering debris from the water and killing bacteria as the water passes through the filter. Other embodiments and refinement of the invention are described herein. The preferred embodiment is described in relation to a water purification material comprising a bacteria killing material and other water purification materials such as algaecides, clarifiers or pH adjusters can be used with the present invention.

SUMMARY OF THE INVENTION

Briefly, the present invention comprises an in situ water purification system comprising a replaceable dual filter having a porous medium for removing debris and a bacteria killing material thereon for killing bacteria while minimizing obstruction to normal flow through the system as well as a process of making a water purification device by dispersibly securing a bacteria killing material to a filter medium for removing debris.

BRIEF DESCRIPTION OF THE DRAWINGS

FIG. 5 is a side view of a portion of a filter medium without a bacteria killing material thereon;

FIG. 6 is a front view of the portion of the filter medium of FIG. 5;

FIG. 9 is a top view a filter cartridge;

FIG. 10 is a sectional view taken along lines 10—10 of FIG. 9 to show the invention of a filter with a bacteria killing material located therein;

FIG. 11 is a perspective view of a filter sleeve that has been formed from a single piece of cloth with the filter stitched and sonic welded into an annular shape;

FIG. 12 is an exploded pictorial view of a filter cartridge housing contain a bacteria killing material.

DESCRIPTION OF THE PREFERRED EMBODIMENT

In the invention described herein, one forms an in situ water purification system comprising a water treatment composition and a filter medium suitable for inserting into a water supply to both kill bacteria therein and to screen debris from the water. In one embodiment the water treatment composition comprises a carrier and a metal ion yielding material which is secured to a filter medium. Attached to the carrier is a bacteria killing material which, in the preferred embodiment, comprises silver chloride (AgCl) coating located thereon. The silver chloride particles are suspended in an adhesive matrix that adhesively secures the silver chloride particles proximate thereto in an ion yielding relationship. Another suitable metal ion yielding material suitable for use is zinc.

The bacteria killing material is preferably a metal ion yielding material although other materials could be used if the materials can be maintained in active mode over an extended period of time. An example of silver ion yielding material is silver chloride which is described more fully in my co-pending application Ser. No. 08/957,265, filed Oct. 24, 1997, titled Water Treatment Composition. Silver chloride is a white powder that can be melted or cast like a metal, and is derived from heating a silver nitrate solution and adding hydrochloric acid or salt solution to produce a silver chloride solution which is then boiled or filtered either in the dark or under a ruby red light to produce the silver chloride powder. In one embodiment of described process, the silver chloride while still in solution is combined with an adhesive to form an adhesive silver chloride solution. The adhesive and the silver chloride solution are then applied to a carrier such as a pellet. The adhesive is then cured to produce a pellet having a silver chloride coating adhesively adhered thereto with both the zinc and the silver chloride available for reacting with the chemicals within a bacteria cell to kill or damage the bacteria.

In a preferred embodiment of process, the silver chloride while still in solution is combined with an adhesive to form an adhesive silver chloride solution which is applied directly to a filter material for use in screening waste particles from a water source. The term adhesively secured herein is meant to include a surface attachment structure that does not prevent the bacteria killing materials from releasing the ions to kill unwanted bacteria.

Figure 1:
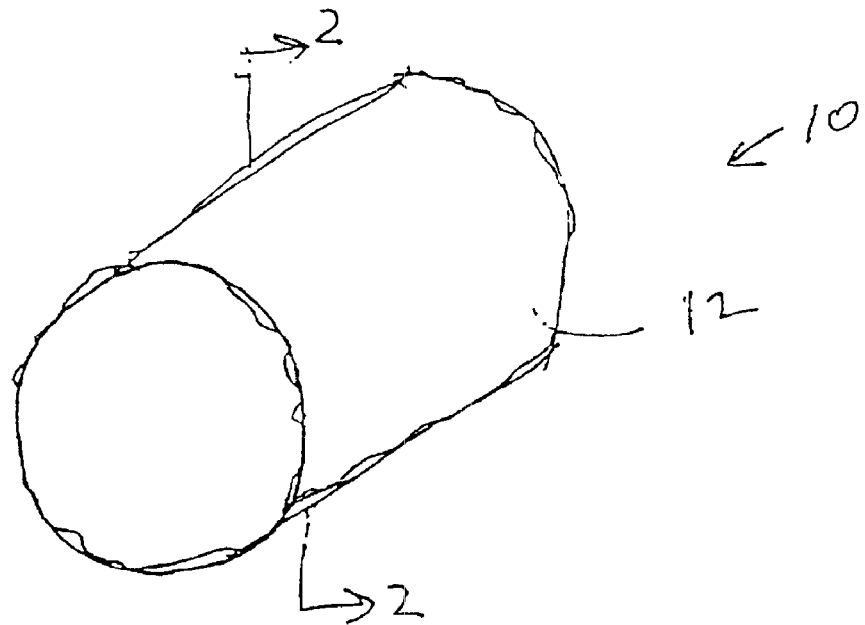
FIG. 1 is a perspective view of a carrier such as zinc pellet having a matrix carrying a silver yielding ion thereon.
Figure 2:
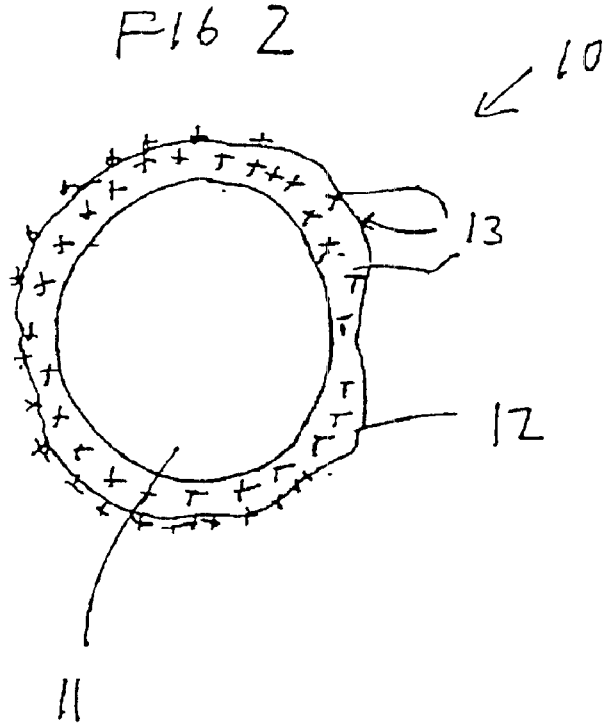
FIG. 2 is a sectional view taken along lines 2—2 of FIG. 1 to show the adhesive matrix located around the zinc pellet.
Figure 3:
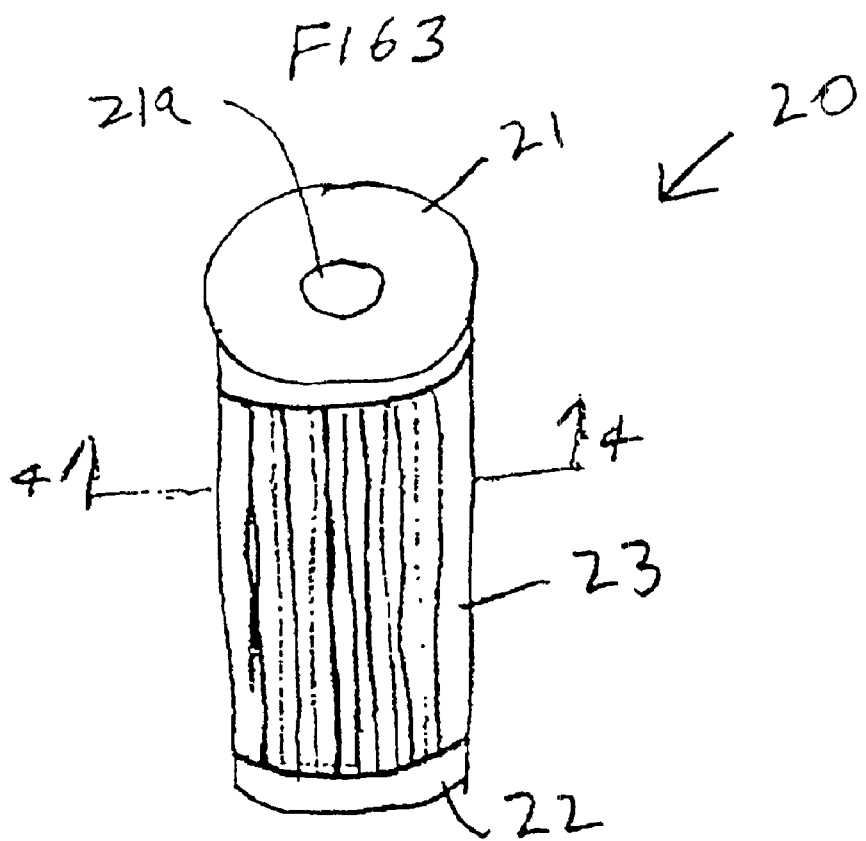
FIG. 3 is a perspective view of a cartridge filter of the present invention.
Figure 4:
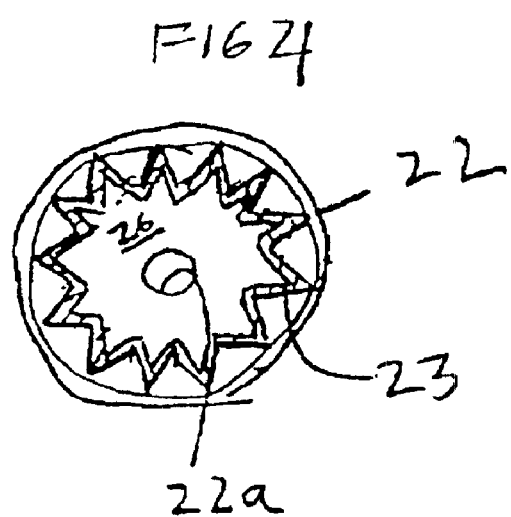
FIG. 4 is a cross-sectional view of the filter of FIG. 1 taken along lines 4—4 of FIG. 3.
Figure 7A:
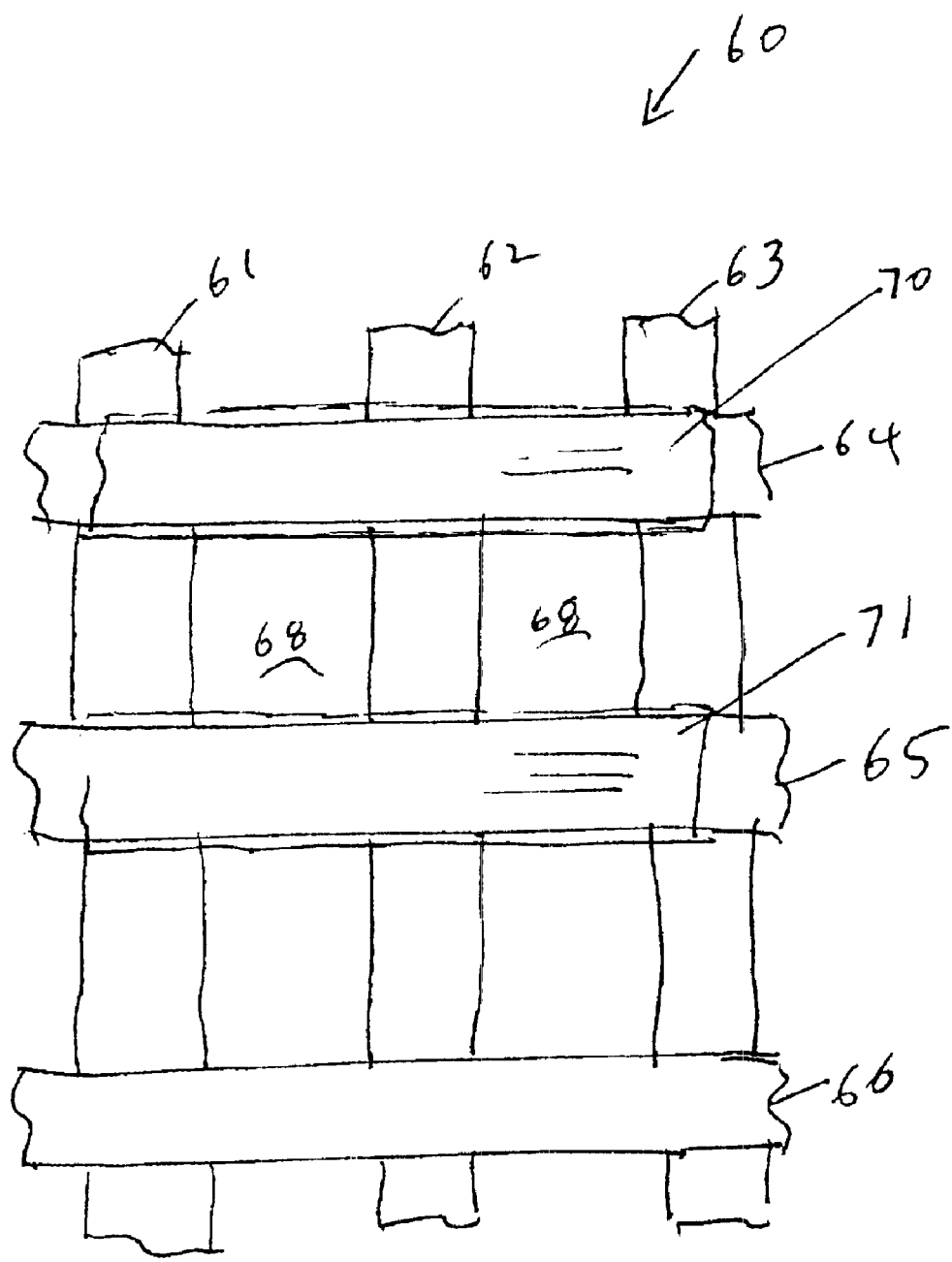
FIG. 7 is front view of a portion of the filter medium of FIG. 6 with a bacteria killing material secured thereto.

Referring to FIGS. 1 and 2, there is shown one way of forming a water treatment pellet 10 having an adhesive matrix coating 12. Adhesive matrix coating 12 comprises an adhesive that secures itself to the surface of both the silver ion generating material, which comprises silver chloride 13 and to the carrier, which is shown as a pellet 11. The process is described in relation to forming a silver chloride coating on a pellet so that the silver ion remains in a reactive state to react with the chemicals in the bacteria and effectively damage or kill the bacteria. However, the carrier 11 could be an active carrier, such as zinc as multiple ion generating material may be suitable for killing different types of bacteria.

FIG. 2 is a cross-sectional view of the silver chloride coated pellet 10 of FIG. 1 showing carrier particle 11 centrally located within adhesive matrix 12 that contains silver chloride 13 dispersed throughout the adhesive matrix 12. As can be seen from the drawing, the silver chloride 13 is maintained in the water porous matrix proximate the carrier pellet 11 to enable water to contact both the silver chloride located within the matrix. These type of pellets 11 can be placed directly into a container in the water to allow the bacteria killing materials to be released into the water. In one embodiment of the present invention the pellets containing the bacteria killing materials are secured directly to a filter medium so that the bacteria killing materials controllable release metal ions over an extended period of time.

In the embodiment shown in FIG. 2 one coats a carrier particle with a silver ion yielding material such as silver chloride by adhesively affixing or securing the silver chloride to the carrier through a non-soluble water porous adhesive matrix. A suitable material for adhesively securing the silver chloride proximate the carrier is commercially available gelatin which can be cross-linked with an aqueous solution of formaldehyde or glutaraldehyde to form a non-soluble, water penetrable matrix on the exterior surface of the carrier. Other suitable non-soluble water porous adhesive matrixes are polyvinyl acetate, polyurethane, epoxy resin, polyvinyl alcohol and polyvinyl acetate.

In the process of forming individual carriers for the ion generating materials, one forms a plurality of carriers or water treatment members typically an ⅛ inch or smaller which are suitable for inserting into an inline feeder. Instead of placing the individual carriers into a separate inline feeder the present invention includes the step of securing the carriers with the ion generating material directly to the filter material used to form a mechanical filter. In the preferred mode of the invention, the ion generating materials are secured directly to the fabric or filter medium without the use of a separate carrier. In both cases one obtains a dual filter system that provides for in situ killing of bacteria and removal of debris from the water flowing through the filter system.

The following examples illustrate how silver chloride particles were affixed proximate to the exterior surface of a carrier such as a pellet.

EXAMPLE 1

In order to coat a batch of pellets with an adhesive matrix containing silver chloride, 12.5 grams of silver nitrate are mixed in 25 ml of distilled water to form an aqueous silver nitrate mixture.

Next, 1.5 grams of gelatin are mixed in 25 ml of distilled water to form a gelatin mixture. The gelatin mixture is heated to a temperature of about 140 degrees F.

To eliminate lumps in the gelatin mixture, the gelatin mixture is then strained through a screen. At this point, 5 grams of sodium chloride are mixed into the gelatin mixture. The gelatin mixture is then combined with the aqueous silver nitrate mixture to convert the silver nitrate into silver chloride to thereby form an aqueous silver chloride gelatin mixture. A batch of pellets having a maximum dimension of about ⅛ inch are then heated to about 140 degrees F. The pellets are then sprayed with the heated, aqueous silver chloride gelatin mixture. In order to form a matrix to affix the silver chloride to the pellets, the silver chloride gelatin mixture is then immersed in an aqueous bath of glutaraldehyde for about 12 hours to react the gelatin with the glutaraldehyde. The curing produce an adhesive matrix that secured the pellets with the silver chloride that is dispersed throughout the adhesive matrix. After curing, the pellets, which are covered with a coating of silver chloride, are rinsed and air dried to produce pellets with a silver chloride coating affixed proximate to the pellets.

EXAMPLE 2

The above process was repeated except instead of immersing the pellets with the silver chloride gelatin mixture in an aqueous bath of formaldehyde, the pellets with the silver chloride gelatin mixture were cured in an aqueous bath of formaldehyde.

In the above examples, the pellets had a maximum dimension of about ⅛ of an inch Larger or smaller pellets could be used; however, for use as a water treatment composition in a dispensing valve, it is preferred to have carrier in multiple pellets in order to present a larger surface area to the water containing the bacteria. While securing of the bacteria killing material to the pellet carrier has been described the bacteria killing material can also be secured directly to the filter medium using the same adhesive.

In the above described method of forming the bacteria killing material, the adhesive used was gelatin as gelatin is capable of adhering to the surfaces of both the carrier and the silver chloride. That is, gelatin which can be cross-linked in the presence of formaldehyde or glutaraldehyde to obtain the necessary adhesive characteristics remains non-soluble in the water and unreactive with either the carrier or the silver chloride, and thus can hold the silver chloride proximate the carrier. That is the cross-linked gelatin not only forms a surface attachment but forms a matrix to support or secure the silver chloride in proximity to the surface of the pellet. As the gelatin matrix is securable to the surfaces of both the silver chloride and to the pellets, one is assured that the silver ion yielding material will remain proximate each other to generate ions thereof. Also, the gelatin is desirable since the porosity of the adhesive matrix formed from gelatin allows bacteria containing water access to both the silver to enable both the silver ions to kill the bacteria in the water.

While gelatin is described as one of the adhesives, other suitable adhesives for securing the bacteria killing material to either the carrier or directly to the filter material so that the metal ions are controllable released include polyurethane, epoxy resin polyvinyl alcohol and polyvinyl acetate.

Referring to FIG. 3, reference numeral 20 identifies a dual filter apparatus of the present invention for simultaneously removing debris and killing bacteria. The filter 20, which is in cartridge form, includes a first end cap 21 and a second end cap 22 with a porous pleated filter medium 23 secured therebetween for screening waste particles from the water as the water flows through the filter medium 23. End cap 21 is shown with an opening 21*a* for ingress of fluid, and similarly FIG. 4 shows that end cap 22 includes an opening 22*a* for ingress of fluid into the interior 26 within the zig-zag shaped filter medium 23.

FIG. 5 and FIG. 6 show a portion of one embodiment of a porous filter medium 30 that is arranged in a cross-hatched pattern to form a network comprised of a set of vertical fibers 31, 32 and 33 supporting a set of horizontal fibers 34, 35, 36, 37 and 38 to provide a plurality of regular openings 39 therein for screening waste particles of larger size from the water. In normal operation of the filter medium 30, water flows though the openings 39 while the large debris particles encounter the external network of fibers and are thus prevented from flowing through the filter medium 30. In time the filter becomes clogged with waste particles and needs to be replaced. In the embodiment of FIG. 5 and FIG. 6 the fibers are shown as round with regular shaped openings therein; however, it should be understood that the shape of the fibers, the shape of the openings as well as the use of non-fibers are suitable for making a filter for removing water carried debris as the water flows through the filter medium.

FIG. 7 shows the filter medium 30 with a bacteria killing material 40 dispersibly secured to the surface of the filter medium so as to minimize obstruction to normal flow through the filter housing. In the embodiment shown, the bacteria killing material comprises silver chloride and a pellet acting as a carrier. By securing the bacteria killing material to the fibers of the filter, one provides protrusions that come into contact with the water that flows through openings 39. Note, the obstruction to normal flow through the filter is minimized since the material does not require a separate container nor is the material concentrated in one region of the filter system. That is, placement of a housing in the core of a filter creates a restriction in a narrowest portion of the system. In the present invention the bacteria killing material is placed in the portion of the system where the volume restriction is the least. That is, the area of the filter medium is large compared to the flow area through the core of the filter. Consequently, sufficient bacteria killing material can be dispersibly secured to the filter medium or proximate the filter medium so that the density of bacteria killing material per unit of flow area of the filter medium is small in comparison to the density of bacteria killing material which is required if the bacteria killing material is located in the core area of the filter. Thus, debris material which is larger than opening 39 is prevented from passing through the filer medium by the network of fibers while the water coming into contact with the bacteria killing material on the fibers receives the bacteria killing action. While only two layers of fibers are shown, it is apparent that multiple layers of fibers can be stacked to provide a torturous path for the water to follow thereby increasing the contact between the water and the bacteria killing material.

FIG. 7*a* shows a portion of the filter medium 60 wherein the separate carrier for the bacteria killing material has been dispensed with. In this preferred mode the portion of the filter medium includes fibrous members 61, 62 and 63 that intersect with members 64, 65 and 66 to form a plurality of openings 68 therethrough. In the embodiment shown the bacteria killing material is dispersibly secured directly to fibers by a thin film of non-water soluble porous adhesive 70 and 71. The adhesive 70 dispersibly secures the bacteria killing materials directly to the fibers of the filter medium in a condition to allow a controlled release of ions. In the embodiment shown, the bacteria killing material is preferably a controllable releasable ion yielding material selected from the group of metal ion yielding materials consisting of zinc sulphate, zinc carbonate, zinc chloride, copper carbonate, copper sulfate, silver chloride, stannous chloride and stannic chloride. Other ion yielding materials with controllable release include copper (II) acetate and its hydrates, copper (I) bromide and its hydrates, copper (II) bromide, copper (I) chloride and its hydrates, copper (II)

chloride and its hydrates, copper (II) gluconate, copper (II) hydroxide, copper (II) oxide, copper sulfate, zinc acetate and its hydrates, zinc bromide and its hydrates, zinc carbonate hydroxide hydrate, zinc carbonate, zinc chloride and its hydrates, zinc citrate and its hydrates, zinc iodide and its hydrates, zinc nitrates and its hydrates, zinc oxide, zinc sulfate and its hydrates, silver acetate, silver carbonate, chelated silver ions, silver-exchanged zeolite, silver nitrate, silver oxide, silver sulfate, silver chloride, silver powder and colloidal silver, silver bromide and silver acetate.

In addition to water purification materials that kill bacteria, other water purification materials such as algaecides, clarifiers or even pH adjustment materials such as limestone can be carried by the present invention to provide the dual action of water screening for waste particles while simultaneously purifying the water.

Figure 8:
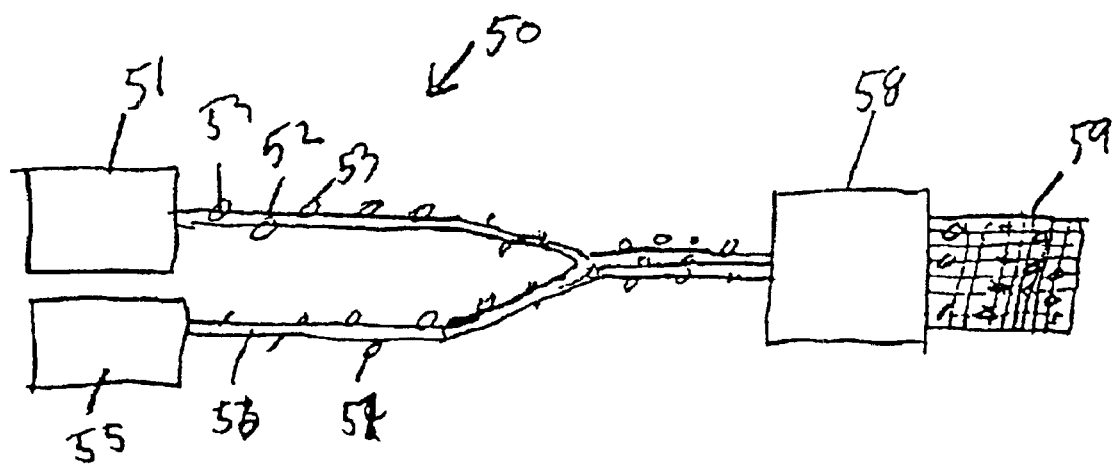
FIG. 8 is a partial schematic view of a system for manufacturing filter medium.

FIG. 8 shows a method of making a filter medium that can simultaneously filter out debris and kill bacteria with two different bacteria killing materials. In the method illustrated in FIG. 8, the filter medium manufacturing system 50 includes a first station 51 for forming a fiber 52 having a plurality of a first bacteria killing materials such as zinc particles 53 secured thereto. A second station 55 includes a second fiber 56 having a second bacteria killing material such as silver chloride particles 57 secured thereto. The fibers are directed into a third station 58 that weaves the fibers into a porous filter medium 59 comprised of fibers with a first bacteria killing material thereon and fibers with a second bacteria killing material thereon which are located in proximity to each other to thereby provide the bacteria killing action from two different bacteria killing materials. Although different embodiments are shown, in each embodiment the filter medium, which normally is used to remove debris from the water by screening the waste particles, is also used as a carrier for the first bacteria killing materials and the second bacteria killing materials which are dispersibly secured thereon so that water passing through the filter medium not only removes debris removed but also the bacteria is killed by the bacteria killing materials located on the filter medium.

FIG. 9 is a top view a filter cartridge 70 and FIG. 10 is a sectional exploded view of filter cartridge 70 taken along lines 10—10. Filter cartridge 70 includes atop cap member 71 and a bottom cap member 72 with a rigid core tube 73 that connects top cap member 71 to bottom cap member 72. A filter medium 75, which is arranged in an annular shape with a series of pleats that extend circumferentially around the exterior of filter cartage 70. Located between core tube 73 is an annular carrier that is impregnated with a bacteria killing material and more particularly to a bacteria killing material that controllable releases metal ions into water flowing through filer medium 75 to thereby effectively kill bacteria. Thus the embodiment shown in FIG. 10 comprises a dual filter apparatus for a swimming pool, hot tub or spa with the filter medium 75 comprising a network of openings therein to enable water to flow therethrough while retaining waste particles. The bacteria killing material, is dispersibly secured in an annular carrier insert 77 proximate the filter medium 75. The bacteria killing material is releasable over time so that the flow path of water through and around annular carrier insert 77 kills bacteria therein while the filter medium 75 removes waste particles to thereby enable the dual filter apparatus to simultaneously remove waste particles and kill bacteria. By having the insert 77 attached to the filter cartridge 70 one can simultaneously replace the bacteria killing material and the filter cartridge. However, if desired the insert could be separately replaceable. Although insert 77 is shown attached to filter cartridge it is envisioned that insert 77 could also be placed directly in the line leading to or away from the filter housing or on the inside of the filter housing and proximate the outside of the filter.

FIG. 11 is a perspective view of a porous filter sleeve 80 that has been formed from a single piece of flexible material with the material containing a sonic weld 81 that holds the material in an annular shape. The single piece of material can form an external sleeve for dispersibly carrying the bacteria killing material. That is, the sleeve 80 includes a porous material that lets debris and water through with a bacteria killing material dispersibly secured thereto. The bacteria killing material is controllable releasable as water flows through the filter sleeve. In operation filter sleeve 80 can be placed on the outside of a filter cartridge to provide the bacteria killing materials to water flowing through the filter cartridge. By placing the proper size sleeve on the cartridge a user can on an after market basis match the life of the filter medium as a screeener of waste particles to the amount of bacteria killing material necessary to kill bacteria during the useful life of the filter so that the filter can simultaneously release screen waster particles and kill bacteria to provide a dual water filter apparatus.

FIG. 12 is a pictorial exploded view of filter cartridge 70 showing the filter core tube 73 with openings 73 therein for flow of water therethrough. Positioned next to core tube 73 is annular sleeve 77 that carries a bacteria killing material dispersed therein that becomes an integral part of the filter. That is annular sleeve 77 sits between core tube 73 and annular filter medium 75. A set of bands 75*a* are located in a spaced condition around the periphery of filter medium 75 to maintain the integrity of the filter medium.

Figure 13:
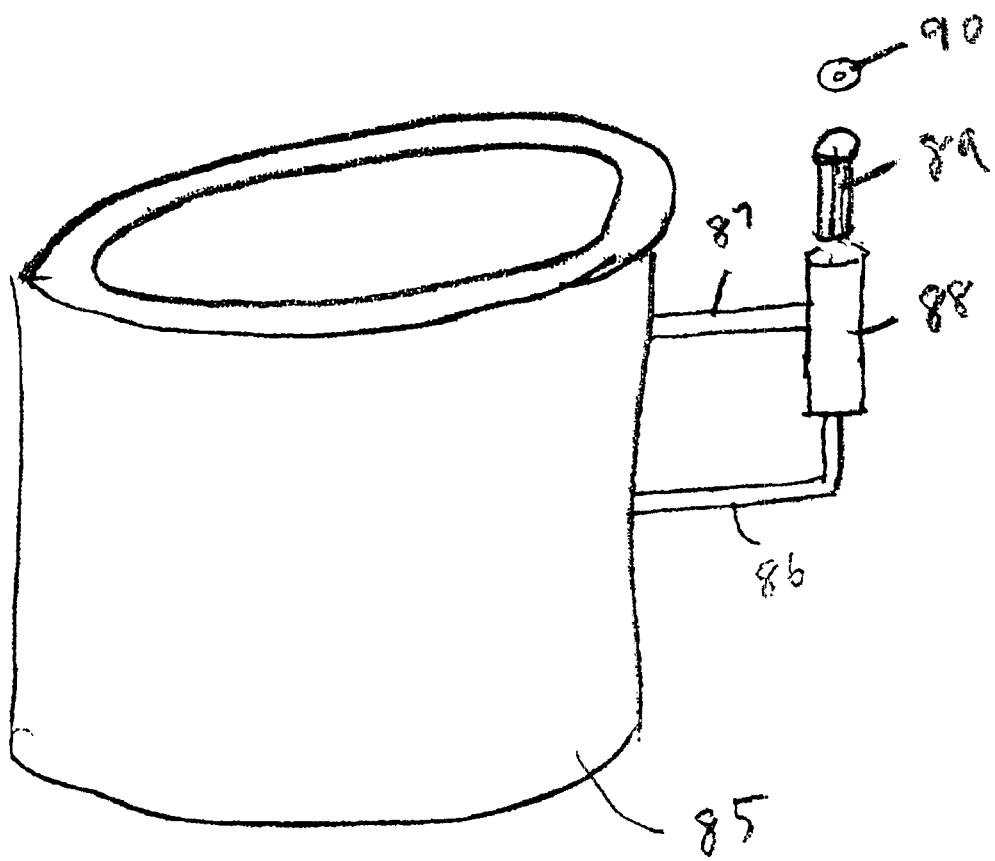
FIG. 13 is partial schematic view of a dual filter system for simultaneously removing debris and killing bacteria.

FIG. 13 is a partial schematic view of a system for water purification wherein debris and bacteria are simultaneously removed by a replaceable cartridge. The water purification system includes a container 85 for holding water to be purified. An outlet 86 direct water to filter housing 88 wherein a cartridge filter 89 having a filter medium with a bacteria killing material secured thereto is located. A cap 90 is placed onto top of container 88 to hold filter cartridge 89 therein. The water circulates back into container 85 through conduit 87. Thus it can be envisioned that the system is suitable for water purification of swimming pools, hot tubs or spas which need to maintain the water free of debris as well as free of harmful bacteria.

While the ion yielding material is shown mechanical secured to the filter medium though an adhesive it is envisioned that in certain types of filters the ion yielding materials could be integrally formed into a portion of a filter medium or a water cartridge housing such as an end cap or the filter core. Thus it is envisioned that the bacteria killing material which is yieldable in the presence of water can be carried either within a porous structure of the housing or a porous structure of the filter medium or dispersibly secured to the filter medium so that the bacteria killing material can be released as water contacts the housing.

Thus in one embodiment of the invention the invention comprises a water filter structure that minimizes obstruction to normal flow through the filter housing. The housing including at least a portion therein containing a water treatment composition that yields a water treatment composition material in the presence of water. A filter medium secured to the cartridge has a network of openings sufficiently large to allowing water to flow therethrough but sufficiently small to prevent waste particles from flowing therethrough so that when water flows through the housing the water treatment composition performs an action to the water while the filter medium screens out waste particles from the water. Examples of water treatment compositions that perform an action include algaecides, bactericide, clarifiers, pH adjusters (for example, limestone) and foam suppressants.

I claim:

1. A method of making a dual filter for in situ water purification that minimizes obstruction to normal flow through a filter housing comprising;

forming a filter medium into a filter cartridge, the filter medium having a network with openings therein for allowing water therethrough but for preventing waste particles from flowing therethrough;

securing a controllable release bacteria killing material to said filter medium to enable said dual filter medium to simultaneously screen waste particles from a water source and kill bacteria that come into contact with the bacteria killing material; and placing the filter cartridge into a filter housing of a water circulation system for a pool, spa or hot tub.

2. The method of claim 1 wherein the step of securing the bacteria killing material comprises dispersing a metal ion yielding material on an extended area of the filter medium to minimize flow obstruction through the filter.

3. The method of claim 2 wherein the step of securing the bacteria killing material comprises securing silver chloride to the filter medium.

4. The method of claim 3 wherein the step of securing the bacteria killing materials comprises securing a second metal ion yielding material to said filter medium.

5. The method of claim 1 wherein the step of securing the bacteria killing material comprises adhesively and dispersibly securing silver chloride to an extended portion of said filter medium to thereby minimize obstruction to normal flow through said filter.

6. The method of claim 1 including the step of securing a further bacteria killing material to the filter medium so that the water carried bacteria come into contact with both the bacterial killing material and the further bacteria killing material to enable both the bacteria killing material and the further bacteria killing material to kill bacteria therein while the filter medium entraps debris thereon.

7. The method of claim 1 wherein the step of securing the bacteria killing material includes using an adhesive to form surface attachment to the bacteria killing material and the filter medium to hold the bacterial killing material in a condition for releasing bacteria killing material therefrom.

8. The method of claim 1 including the step of forming a plurality of fibers having a bacteria killing material thereon and then forming the plurality of fibers into the filter medium.

* * * * *